US011136417B2

(12) United States Patent
Miuchi et al.

(10) Patent No.: US 11,136,417 B2
(45) Date of Patent: *Oct. 5, 2021

(54) LOW MOLECULAR GUM GHATTI

(71) Applicant: SAN-EI GEN F.F.I., INC., Toyonaka (JP)

(72) Inventors: Takeshi Miuchi, Osaka (JP); Takuma Matsukura, Osaka (JP); Ryo Maruyama, Osaka (JP); Keigo Kinoshita, Osaka (JP)

(73) Assignee: SAN-EI GEN F.F.I., INC., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/337,755

(22) PCT Filed: Sep. 29, 2017

(86) PCT No.: PCT/JP2017/035739
§ 371 (c)(1),
(2) Date: Mar. 28, 2019

(87) PCT Pub. No.: WO2018/062554
PCT Pub. Date: Apr. 5, 2018

(65) Prior Publication Data
US 2019/0389980 A1 Dec. 26, 2019

(30) Foreign Application Priority Data
Sep. 30, 2016 (JP) .............................. JP2016-195238

(51) Int. Cl.
*C08B 37/08* (2006.01)
*A61K 8/06* (2006.01)
*A61K 8/73* (2006.01)
*C08J 3/11* (2006.01)
*C08J 3/14* (2006.01)
*C08B 37/00* (2006.01)
*C08K 5/103* (2006.01)

(52) U.S. Cl.
CPC ............ *C08B 37/0087* (2013.01); *A61K 8/06* (2013.01); *A61K 8/73* (2013.01); *C08J 3/11* (2013.01); *C08J 3/14* (2013.01); *C08K 5/103* (2013.01)

(58) Field of Classification Search
CPC ...... A61K 8/06; A61K 8/73; C08J 3/11; C08J 3/14; C08B 37/00; C08B 37/0087
USPC .......................................................... 514/54
See application file for complete search history.

(56) References Cited

U.S. PATENT DOCUMENTS

| 3,353,961 A | 11/1967 | Simon et al. |
| 3,891,620 A * | 6/1975 | Cushman ............... A61K 47/36 536/3 |
| 4,581,256 A | 4/1986 | Sommer |
| 5,725,605 A | 3/1998 | Maunz et al. |
| 6,477,982 B1 | 11/2002 | Ritter |
| 8,460,734 B2 | 6/2013 | Sakata et al. |
| 8,846,126 B2 | 9/2014 | Baseeth et al. |
| 9,737,088 B2 | 8/2017 | Endo et al. |
| 2005/0096464 A1 | 5/2005 | Heikkila et al. |
| 2005/0124805 A1 | 6/2005 | Al-Assaf et al. |
| 2007/0286930 A1 | 12/2007 | Ogawa et al. |
| 2008/0124437 A1 | 5/2008 | Fang et al. |
| 2008/0249000 A1 | 10/2008 | Sakata et al. |
| 2009/0004304 A1 | 1/2009 | Ikehara et al. |
| 2009/0117238 A1 | 5/2009 | Ido et al. |
| 2010/0020385 A1 | 1/2010 | Yamamoto et al. |
| 2010/0034956 A1 | 2/2010 | Yasumi et al. |
| 2011/0033555 A1 | 2/2011 | Kwetkat et al. |
| 2011/0274812 A1 | 11/2011 | Nakauma et al. |
| 2012/0100251 A1 | 4/2012 | Baseeth et al. |
| 2013/0095221 A1 | 4/2013 | Baseeth et al. |
| 2013/0108763 A1 | 5/2013 | Saitoh et al. |
| 2013/0115345 A1 | 5/2013 | Miuchi et al. |
| 2014/0242246 A9 | 8/2014 | Baseeth et al. |
| 2014/0370154 A1 | 12/2014 | Sakata et al. |
| 2015/0017306 A1 | 1/2015 | Harada et al. |
| 2015/0045453 A1 | 2/2015 | Endo et al. |

FOREIGN PATENT DOCUMENTS

| CN | 1771263 | 5/2006 |
| CN | 101945698 | 1/2011 |
| CN | 102946866 | 2/2013 |
| CN | 102958372 | 3/2013 |
| CN | 104961840 | 10/2015 |
| EP | 2721933 | 4/2014 |
| JP | H02-042943 | 2/1990 |
| JP | H08-140623 | 6/1996 |
| JP | 2006-257246 | 9/2006 |
| JP | 2006-522202 | 9/2006 |
| JP | 2007-014288 | 1/2007 |
| JP | 2007-049908 A * | 3/2007 ............ A23L 1/207 |
| JP | 2007-151480 A | 6/2007 |

(Continued)

OTHER PUBLICATIONS

Amar et al, Foods and Food Ingredients Journal of Japan, 2006, 211(3), 275-280.*

Ido et al, FFI Journal, 2008, 213(4), 365-370.*

International Search Report (Japanese and English) issued for International Application No. PCT/JP2017/035739, dated Dec. 19, 2017, 5 pages.

Ido (San-Ei Gen F.F.I., Inc.), FFI Reports, Foods & Food Ingredients Journal of Japan, 2006, vol. 211, No. 7, pp. 641-645. Description of relevance in International Search Report.

Amar, V., et al., "The Structure and Function of Arabinogalactan Proteins (AGPs) (2), An Introduction to Gum Ghatti: Another Proteinaceous Gum," Foods & Food Ingredients Journal of Japan, 2006, vol. 211, No. 3, pp. 275-280.

(Continued)

*Primary Examiner* — Ganapathy Krishnan

(74) *Attorney, Agent, or Firm* — Hamre, Schumann, Mueller & Larson, P.C.

(57) ABSTRACT

An object of the present invention is to provide an excellent emulsifier. This object is achieved by a low-molecular gum ghatti having a weight average molecular weight within the range of $0.020 \times 10^6$ to $1.10 \times 10^6$.

3 Claims, No Drawings

(56) References Cited

FOREIGN PATENT DOCUMENTS

| | | |
|---|---|---|
| JP | 2007-289124 | 11/2007 |
| JP | 2008-013751 | 1/2008 |
| JP | 2008-094806 | 4/2008 |
| JP | 2011-041512 | 3/2011 |
| JP | 2013-009667 | 1/2013 |
| JP | 5576539 B1 | 8/2014 |
| JP | 2015-023843 | 2/2015 |
| JP | 2016-187344 | 11/2016 |
| WO | 85/00005 | 1/1985 |
| WO | 2004/089991 | 10/2004 |
| WO | 2005/092930 | 10/2005 |
| WO | 2006/126472 A1 | 11/2006 |
| WO | 2009/001786 | 12/2008 |
| WO | 2009/016362 | 2/2009 |
| WO | 2009/147158 | 12/2009 |
| WO | 2010/082570 A1 | 7/2010 |
| WO | 2011/127163 | 10/2011 |
| WO | 2013/084518 A1 | 6/2013 |
| WO | 2013/146181 | 10/2013 |
| WO | 2013/146387 | 10/2013 |
| WO | 2017/017248 | 2/2017 |

OTHER PUBLICATIONS

Cheng Liu, et al., "Practical Encyclopedia of Food Additives", Edition 1, 2004, Beijing Industry University Press, p. 580; Cited in the attached Chinese Office Action, English abstract provided.
Zhenyou Ma, et al., "Skin Beauty Cosmetics Preparation Manual", Edition 2, 2015, Ancient Chinese Medicine Books, p. 366; Cited in the attached Chinese Office Action, English abstract provided.
Agricultural Dictionary, Edition 1, 1998, Agricultural Dictionary Editorial Committee, China Agriculture Press, p. 1523; Cited in the attached Chinese Office Action, English abstract provided.
Office Action issued for the corresponding CN patent application No. 201780060091.X, dated Nov. 3, 2020, 26 pages including English translation.
International Search Report of PCT/JP2018/013923, dated Jun. 12, 2018, 5 pages including English translation.
Ido, T. et al., "Natural Hydrocolloid Emulsifiers (2) Emulsification Properties of Gatifolia (Gum Ghatti) Used for Emulsions in Food Products," Foods & Food Ingred J Jpn, 2008, vol. 213, No. 4, pp. 365-371.
International Search Report of PCT/JP2018/044328, dated Feb. 5, 2019, 5 pages including English translation.
Supplementary Extended European Search Report for the corresponding European patent application No. 17856501.6, dated Jan. 18, 2021, 8 pages.
U.S. Appl. No. 16/499,123, filed Sep. 27, 2019.
U.S. Appl. No. 16/767,955, filed May 28, 2020.
Sharma S C, "Gums and Hydrocolloids in Oil-Water Emulsions", Food Technology, 1981, pp. 59-67.
Riaz R A et al., "Utilization of Stabilizers and Thickeners as Additives in Food Industry", Science and Industry, 1971, vol. 8, No. 1, pp. 17-21.
Katayama et al., "Natural Hydrocolloid Emulsifiers (2), Characteristics of the Adsorbed Component of Gum Ghatti Responsible for Its Oil-Water Interface Advantages", Shokuhin-Shokuhin-Tenkabutsu-kenkyushi, Foods & Food Ingredients Journal of Japan, 2008, vol. 213, No. 4, pp. 372-376.
The extended European Search Report for the related European patent application No. 18792158.0, dated Apr. 7, 2020, 10 pages.
International Search Report of PCT/JP2018/017285, dated Jul. 17, 2018, 2 pages.
International Preliminary Report on Patentability issued for PCT/JP2018/017285, dated Nov. 7, 2019, 8 pages.
U.S. Appl. No. 16/609,047, filed Oct. 28, 2019.
Office Action issued for the related Chinese patent application No. 201880035331.5., dated Jun. 29, 2021, 26 pages including English translation.

* cited by examiner

LOW MOLECULAR GUM GHATTI

TECHNICAL FIELD

The present invention relates to low-molecular gum ghatti.

BACKGROUND ART

Gum ghatti, which has a high molecular weight, can be used as an excellent emulsifier. For example, PTL 1 suggests an emulsion composition prepared using gum ghatti. However, there is still demand for the development of much better emulsifiers. PTL 2 discloses sugar beet pectin with a higher molecular weight than typical sugar beet pectin as an excellent emulsifier.

CITATION LIST

Patent Literature

PTL 1: WO2013/084518
PTL 2: WO2010/082570

SUMMARY OF INVENTION

Technical Problem

An object of the present invention is to provide an excellent emulsifier.

Solution to Problem

In line with the disclosure of PTL 2, it is common technical knowledge that high-molecular emulsifiers typically exhibit higher interfacial activity (or emulsifying capacity) when having a higher molecular weight. Thus, efforts have been made to not reduce the molecular weight of high-molecular emulsifiers, for example, in a purification step.

However, the present inventors conducted extensive research and found that the emulsifying capacity of gum ghatti, which is a known high-molecular emulsifier, can be surprisingly increased by reducing the molecular weight of the gum ghatti, and they completed the present invention on the basis of this finding.

The present invention includes the following subject matter.
Item 1. A low-molecular gum ghatti having a weight average molecular weight within the range of $0.020 \times 10^6$ to $1.10 \times 10^6$.
Item 2. The low-molecular gum ghatti according to Item 1, having a molecular weight distribution, which is a ratio of a weight average molecular weight to a number average molecular weight, within the range of 1.1 to 13.
Item 3. The low-molecular gum ghatti according to Item 1 or 2, wherein emulsified particles have a median size, on a volume basis, within the range of 0.1 to 1.5 μm,
the median size being measured by the following interfacial activity measurement method:
(1) 10 mass % of a medium-chain triglyceride, 35 mass % of an 8 mass % gum ghatti aqueous solution, and 5 mass % of ion-exchanged water are stirred at room temperature, and 50 mass % of glycerol is added thereto to prepare a mixture;
(2) the mixture is subjected to an emulsification treatment at 45 MPa three times with a high-pressure homogenizer to obtain an emulsion; and
(3) a particle size of emulsified particles contained in the emulsion is measured with a laser diffraction/scattering particle size distribution analyzer to determine the median size on a volume basis.
Item 4. A method for producing the low-molecular gum ghatti of any one of Items 1 to 3,
the method comprising subjecting gum ghatti to a molecular weight reduction treatment.
Item 5. The method for producing the low-molecular gum ghatti according to Item 4, wherein the molecular weight reduction treatment includes at least one treatment selected from the group consisting of thermolysis, acidolysis, and enzymatic degradation.
Item 6. A method for increasing interfacial activity of gum ghatti,
the method comprising subjecting gum ghatti to a molecular weight reduction treatment.
Item 7. A method for dispersing a water-insoluble substance,
the method comprising mixing an aqueous liquid, a water-insoluble substance, and the low-molecular gum ghatti of any one of Items 1 to 3.
Item 8. An emulsification method comprising mixing an aqueous liquid, an oil liquid, and the low-molecular gum ghatti of any one of Items 1 to 3.
Item 9. A method for producing a dispersion composition,
the method comprising mixing an aqueous liquid, a water-insoluble substance, and the low-molecular gum ghatti of any one of Items 1 to 3.
Item 10. A method for producing an emulsion composition,
the method comprising mixing an aqueous liquid, an oil liquid, and the low-molecular gum ghatti of any one of Items 1 to 3.
Item 11. A composition comprising the low-molecular gum ghatti of any one of Items 1 to 3.
Item 12. The composition according to Item 11, which is an emulsifier or a dispersant.
Item 13. The composition according to Item 11, which is a dispersion composition.
Item 14. The composition according to any one of Items 11 to 13, which is a food or drink, a cosmetic or fragrance, a medical drug, or a quasi-drug.

Advantageous Effects of Invention

The present invention provides an excellent emulsifier.

DESCRIPTION OF EMBODIMENTS (1) Terms

The symbols and abbreviations used in the present specification are understood as referring to typical meanings used in the technical field to which the present invention pertains, depending on the context of the present specification, unless otherwise limited.

In the present specification, the term "comprise" is intended to include the meaning of the term "consist essentially of" and the term "consist of."

Unless otherwise limited, the step, treatment, or operation described in the present specification is performed at room temperature.

In the present specification, room temperature refers to a temperature within the range of 10 to 40° C.

In the present specification, the term "derived" is intended to include the following meanings:
(i) purified,
(ii) isolated, and
(iii) altered (including a treatment for reducing molecular weight and a treatment for increasing molecular weight (polymerization)) or modified.

In the present specification, the term "interfacial activity" and the term "emulsifying capacity" are interchangeably used, depending on the context.

(2) Low-Molecular Gum Ghatti

In the present specification, the term "gum ghatti" refers to a polysaccharide derived from tree sap (succus) of *Anogeissus latifolia Wallich*, and is a water-soluble polysaccharide that typically dissolves in water at room temperature or higher to the degree of about 30 mass %.

In the present specification, gum ghatti includes "low-molecular gum ghatti."

The low-molecular gum ghatti according to the present invention must have a weight average molecular weight of $0.020 \times 10^6$ to $1.10 \times 10^6$, and preferably has a weight average molecular weight of $0.020 \times 10^6$ to $0.90 \times 10^6$, more preferably $0.020 \times 10^6$ to $0.60 \times 10^6$, still more preferably $0.025 \times 10^6$ to $0.50 \times 10^6$, even more preferably $0.030 \times 10^6$ to $0.40 \times 10^6$, particularly preferably $0.030 \times 10^6$ to $0.30 \times 10^6$, and even more particularly preferably $0.040 \times 10^6$ to $0.30 \times 10^6$.

Due to such a weight average molecular weight, the low-molecular gum ghatti according to the present invention can have high interfacial activity (or emulsifying capacity).

The low-molecular gum ghatti according to the present invention preferably has a molecular weight distribution (the ratio of the weight average molecular weight to the number average molecular weight) (Mw/Mn) of 1.1 to 13, more preferably 1.1 to 10, still more preferably 1.1 to 8, even more preferably 1.1 to 6, and particularly preferably 1.1 to 4.

The molecular weight and its distribution of gum ghatti of the present invention are measured in accordance with the following method.

Method for Measuring Molecular Weight and Molecular Weight Distribution

The molecular weight and molecular weight distribution are measured by GPC analysis under the following conditions.
Detector: RI
Mobile Phase: 100 mM $K_2SO_4$
Flow Rate: 1.0 ml/min
Temperature: 40° C.
Column: TSKgel GMPWXL 30 cm (Guard PWXL)
Injection: 100 μl
Pullulan Standard: Shodex STANDARD P-82

(2-1) The Properties of Low-Molecular Gum Ghatti According to the Present Invention (2-1-1) Interfacial Activity The low-molecular gum ghatti according to the present invention functions as an emulsifier and can form emulsified particles. The interfacial activity of an emulsifier can be evaluated on the basis of the size of emulsified particles formed by using the emulsifier. The interfacial activity (or emulsifying capacity) increases with a decrease in size of the emulsified particles. The low-molecular gum ghatti according to the present invention exhibits the following median size (on a volume basis) of emulsified particles measured by an interfacial activity measurement method described below: a median size of preferably 0.1 to 1.5 μm, more preferably 0.1 to 1.2 μm, still more preferably 0.1 to 1 μm, even more preferably 0.2 to 0.9 μm, particularly preferably 0.2 to 0.85 μm, particularly more preferably 0.2 to 0.83 μm, and even more particularly preferably 0.2 to 0.8 μm.

The fact that the low-molecular gum ghatti according to the present invention can exhibit such a small median size of emulsified particles indicates that the low-molecular gum ghatti according to the present invention has high interfacial activity (or an emulsifying capacity).

Interfacial Activity Measurement Method (1) 10 mass % of a medium-chain triglyceride, 35 mass % of an 8 mass % gum ghatti aqueous solution, and 5 mass % of ion-exchanged water are stirred at room temperature, and 50 mass % of glycerol is added thereto to prepare a mixture;
(2) the mixture is subjected to an emulsification treatment at 45 MPa three times with a high-pressure homogenizer to obtain an emulsion; and
(3) the particle size of emulsified particles contained in the emulsion is measured with a laser diffraction/scattering particle size distribution analyzer to determine the median size (on a volume basis).

The high pressure homogenizer for use is a Nanomizer or an equivalent apparatus.

(2-1-2) the Viscosity of a Low-Molecular Gum Ghatti Aqueous Solution

The low-molecular gum ghatti aqueous solution according to the present invention may have the following viscosity.

The Viscosity of an 8 Mass % Aqueous Solution (the Viscosity According to Measurement Method A)

An 8 mass % aqueous solution of the low-molecular gum ghatti according to the present invention (20° C.) preferably exhibits the following viscosity as measured by measurement method A described in the Examples below: a viscosity of preferably 70 mPa·s or less, more preferably 60 mPa·s or less, still more preferably 50 mPa·s or less, even more preferably 40 mPa·s or less, particularly preferably 35 mPa·s or less, and particularly more preferably 30 mPa·s or less.

The lower limit of the viscosity may be, for example, 1 mPa·s, 2 mPa·s, 3 mPa·s, 4 mPa·s, or 5 mPa·s.

(2-1-3) the Viscosity of a Low-Molecular Gum Ghatti Aqueous Solution

The Viscosity of a 15 wt % Aqueous Solution (the Viscosity According to Measurement Method B)

A 15 wt % aqueous solution of the low-molecular gum ghatti according to the present invention (20° C.) preferably exhibits the following viscosity as measured by measurement method B described in the Examples below: a viscosity of preferably less than 100 mPa·s, more preferably less than 80 mPa·s, still more preferably less than 70 mPa·s, even more preferably less than 60 mPa·s, particularly preferably less than 50 mPa·s, and particularly more preferably less than 40 mPa·s.

The lower limit of the viscosity may be, for example, 10 mPa·s, 20 mPa·s, or 30 mPa·s.

The Viscosity of a 30 wt % Aqueous Solution (the Viscosity According to Measurement Method C)

A 30 wt % aqueous solution of the low-molecular gum ghatti according to the present invention (20° C.) preferably exhibits the following viscosity as measured by measurement method C described in the Examples below: a viscosity of preferably 8000 mPa·s or less, more preferably 5000 mPa·s or less, still more preferably 3000 mPa·s or less, even more preferably 2000 mPa·s or less, particularly preferably 1500 mPa·s or less, particularly more preferably 1000 mPa·s or less, and even more particularly preferably 800 mPa·s or less.

The lower limit of the viscosity may be, for example, 10 mPa·s, 30 mPa·s, 50 mPa·s, 80 mPa·s, or 100 mPa·s.

(2-1-3) The Optical Properties of a Low-Molecular Gum Ghatti Aqueous Solution

The low-molecular gum ghatti aqueous solution according to the present invention can have the following optical properties.

The Turbidity of an Aqueous Solution

A 1 mass % aqueous solution of the low-molecular gum ghatti according to the present invention (20° C.) exhibits the following turbidity (1% E) as measured by a measurement method described below: a turbidity of preferably 0.001 to 0.3, more preferably 0.005 to 0.2, still more preferably 0.008 to 0.1, even more preferably 0.01 to 0.08, particularly preferably 0.015 to 0.07, and particularly more preferably 0.02 to 0.06.

Measurement Method

A 1 mass % aqueous solution of a gum ghatti sample (20° C.) is prepared, and the turbidity (absorbance) at 720 nm is measured with a spectrophotometer (cell: quartz cell, 10 mm×10 mm).

Measurement Instrument: Spectrophotometer (JASCO Corporation, V-660 Spectrophotometer)

(2-2) The Viscosity of an Emulsion

An emulsion prepared using the low-molecular gum ghatti according to the present invention has a suitably low viscosity and has the following viscosity as measured by the viscosity measurement method described below: a viscosity of preferably 1 to 500 mPa·s, more preferably 1 to 250 mPa·s, still more preferably 1 to 160 mPa·s, and even more preferably 1 to 100 mPa·s.

Emulsion Viscosity Measurement Method 80 g of a sample (an emulsion) prepared by the interfacial activity measurement method described above is placed in a 100-mL screw bottle (inner diameter: 3.7 cm), and the viscosity is measured with the following instrument under the following conditions.

Instrument and Conditions

B-type viscometer (Brookfield viscometer), rotor No. 2
Rotation frequency: 30 rpm
Measurement temperature: 20° C.

(2-3) The Turbidity of an Emulsion

An emulsion prepared using the low-molecular gum ghatti according to the present invention has a low turbidity as measured by the following turbidity measurement method (i.e., high transparency), and exhibits high stability of the transparency.

The turbidity (0.1% E) at the time an emulsion is prepared is preferably 0.01 to 0.38, more preferably 0.01 to 0.35, still more preferably 0.01 to 0.3, even more preferably 0.01 to 0.25, and particularly preferably 0.01 to 0.2.

Turbidity Measurement Method

The turbidity of a 0.1% water-dilution solution of a sample (emulsion) prepared by the interfacial activity measurement method described above is measured at 720 nm with a spectrophotometer (cell: quartz cell 10 mm×10 mm).

After being allowed to stand at 60° C. for 3 days, the emulsion containing the low-molecular gum ghatti according to the present invention has a turbidity (0.1% E) of preferably 0.01 to 0.39, more preferably 0.01 to 0.37, still more preferably 0.01 to 0.35, even more preferably 0.01 to 0.33, particularly preferably 0.01 to 0.30, and even more particularly preferably 0.01 to 0.25.

After being allowed to stand at 60° C. for two weeks, the emulsion containing the low-molecular gum ghatti according to the present invention has a turbidity (0.1% E) of preferably 0.01 to 0.39, more preferably 0.01 to 0.37, still more preferably 0.01 to 0.35, even more preferably 0.01 to 0.33, particularly preferably 0.01 to 0.30, and even more particularly preferably 0.01 to 0.28.

(3) The Method for Producing Low-Molecular Gum Ghatti

The low-molecular gum ghatti according to the present invention can be produced by, for example, the production method described below or a similar method.

The method for producing low-molecular gum ghatti according to the present invention comprises subjecting gum ghatti, which is a raw material, to a molecular weight reduction treatment.

Gum ghatti usable as a raw material includes commercially available gum ghatti. Examples of commercially available gum ghatti products include Gum Ghatti SD (San-Ei Gen F.F.I., Inc.). Gum ghatti distributed in the market typically has a weight average molecular weight of $1.1 \times 10^6$ to $2 \times 10^6$. Gum ghatti for use as a raw material is not particularly limited, as long as gum ghatti having a desired molecular weight can be produced; and gum ghatti for use as a raw material originally may partly contain low-molecular weight gum ghatti. For example, gum ghatti as a raw material may contain gum ghatti molecular fractions having a weight average molecular weight exceeding $0.020 \times 10^6$ (preferably a weight average molecular weight more than $0.025 \times 10^6$, more preferably more than $0.030 \times 10^6$, and still more preferably more than $0.080 \times 10^6$).

The method of the molecular weight reduction treatment in this production method is not particularly limited, and preferable examples include molecular weight reduction treatment methods performed in the presence of water, such as at least one treatment selected from the group consisting of thermolysis, acidolysis, and enzymatic degradation.

Thermolysis can be performed by suitably selecting the conditions under which gum ghatti having a desired weight average molecular weight can be obtained on the basis of common technical knowledge. Typically, the higher the treatment temperature, the lower the weight average molecular weight of the obtained gum ghatti. Specifically, the treatment temperature for thermolysis is, for example, 60 to 200° C., and preferably 80 to 200° C.

Typically, the longer the treatment time, the lower the weight average molecular weight of the obtained gum ghatti. Specifically, the treatment time for thermolysis is, for example, 0.01 to 8 hours. The treatment time can be suitably selected, depending on the treatment temperature of thermolysis. For example, a shorter treatment time can be suitably selected for a higher treatment temperature.

Thermolysis can be suitably performed, for example, at a pH of 5 or less.

Examples of acids for use in acidolysis include citric acid (including anhydrous citric acid), phosphoric acid, phytic acid, malic acid, tartaric acid, hydrochloric acid, acetic acid, lactic acid, and ascorbic acid. These acids may be used singly or in a combination of two or more.

Typically, the higher the treatment temperature, the lower the weight average molecular weight of the obtained gum ghatti. The treatment temperature for acidolysis is, for example, 60 to 200° C.

Typically, the longer the treatment time, the lower the weight average molecular weight of the obtained gum ghatti. The treatment time for acidolysis is, for example, 0.01 to 8 hours.

Acidolysis can be suitably performed, for example, at a pH of 4 or less.

Examples of enzymes for use in enzymatic degradation include cellulase; mannanase; pectinase; sucrase; hemicellulase; cellrosin AC40, cellrosin HC100, cellrosin TP25, and cellrosin GM5 (all are trade names, HBI Enzymes Inc.); Sumizyme PX and Sumizyme AG2-L (both are trade names, Shin Nihon Chemical Co., Ltd.); Macerozyme A (trade name, Yakult Pharmaceutical Industry Co., Ltd.); and Macerating Enzyme Y (trade name, Yakult Pharmaceutical Industry Co., Ltd.). These enzymes may be used singly or in a combination of two or more. The conditions for the enzyme treatment (e.g., temperature, time, pH, and additives) can be suitably selected, depending on the enzyme for use.

(4) The Method for Increasing the Interfacial Activity of Gum Ghatti

The present invention also provides a method for increasing the interfacial activity of gum ghatti.

The method for increasing the interfacial activity of gum ghatti according to the present invention comprises subjecting gum ghatti to a molecular weight reduction treatment. The molecular weight reduction treatment may be the same as the molecular weight reduction treatment described for the method for producing gum ghatti.

(5) The Method for Dispersing a Water-Insoluble Substance

The present invention also provides a method for dispersing a water-insoluble substance, more specifically, a method for dispersing a water-insoluble substance in an aqueous liquid. The method for dispersing a water-insoluble substance according to the present invention comprises mixing a water-insoluble substance with an aqueous liquid and the low-molecular gum ghatti according to the present invention.

(5-1) Water-Insoluble Substance

In the present specification, the term "water-insoluble" means solubility in water at 20° C. of less than 1 g/L (preferably less than 0.5 g/L). The form of the water-insoluble substance is not particularly limited. The water-insoluble substance may be in the form of, for example, liquid (e.g., oil liquid) or solid (e.g., a solid of a water-insoluble substance or a hydrophobic solid). In the present invention, the hydrophobic solid has a water contact angle (2 μl, 20° C.) of 90° or more (preferably 120° or more and more preferably 150° or more) on its surface.

The water-insoluble substance may be, for example, (1-1) an oil-soluble material, (1-2) an oil solvent, (1-3) an oil solution formed by dissolving the oil-soluble material in the oil solvent, or (1-4) an inorganic or organic solid salt (e.g., iron pyrophosphate, calcium carbonate, and calcium phosphate); or (1-5) a combination of two or more of them (e.g., a mixture and a composite).

(5-1-1) Oil-Soluble Material (1-1)

In the present specification, the term "oil-soluble" means that the solubility at 20° C. in n-hexane or ethyl acetate, or in both, is 10 g/L or more (preferably 50 g/L). The oil-soluble material is not limited, and includes oil-soluble flavorings, oil-soluble pigments, and oil-soluble physiological active substances.

(5-1-1-1) Oil-Soluble Flavoring

The oil-soluble flavoring (including liposoluble flavorings; the same applies below) usable in the present invention is not limited, as long as the oil-soluble flavoring is an oil-soluble or liposoluble substance containing an aroma component. The oil-soluble flavoring is preferably an edible flavoring that can be added to food or drink, or a flavoring that is applicable to a human body as a cosmetic.

Examples of oil-soluble flavorings include (1) extracts obtained by extraction with a non-volatile solvent, extraction with a volatile solvent, or supercritical extraction from a natural ingredient derived from an animal or plant; (2) natural flavorings, such as essential oils or recovery essences, obtained by a technique such as steam distillation or a press method; (3) synthetic flavorings synthesized by a chemical technique; and (4) flavoring bases obtained by adding or dissolving these flavorings in fat and oil or a solvent.

Examples of natural flavorings include extracts, such as absolutes, extracts, and oleoresins; essential oils, such as cold-pressed oils; and alcohol extracts called tincture.

Specific examples of the flavorings include (1) citrus essential oils, such as orange oil, lemon oil, grapefruit oil, lime oil, and mandarin oil; (2) flower oils or absolutes, such as lavender oil; essential oils, such as peppermint oil, spearmint oil, and cinnamon oil; (3) essential oils or oleoresins of spice, such as allspice, anise seed, basil, laurel, cardamom, celery, clove, garlic, ginger, mustard, onion, paprika, parsley, and black pepper; synthetic flavorings, such as limonene, linalool, geraniol, menthol, eugenol, and vanillin; (4) extract oils derived from beans, such as coffee, cacao, vanilla, and roasted peanut; (5) extracts, such as of black tea, green tea, and oolong tea; and other synthetic flavoring compounds. These flavorings can be used individually, but are typically used as a blended flavoring prepared by combining any two or more flavorings. The term "flavoring" in the present invention is defined as including not only flavorings composed of a single compound but also blended flavorings described above.

(5-1-1-2) Oil-Soluble Pigment

The oil-soluble pigment (including liposoluble pigments; the same applies below) usable in the present invention is not limited, as long as the oil-soluble pigment is an oil-soluble or liposoluble substance containing a coloring component. The oil-soluble pigment is preferably an edible pigment that can be added to food or drink, or a pigment that is applicable to a human body as a cosmetic.

The oil-soluble pigment includes paprika pigment, annatto pigment, tomato pigment, marigold pigment, turmeric pigment, Haematococcus algae pigment, *dunaliella* carotene, carrot carotene, palm oil carotene, α-carotene, β-carotene, astaxanthin, canthaxantin, lycopene, lutein, apocarotenal, curcumin, fucoxanthin, cryptoxanthin, zeaxanthin, capsanthin, capsorubin, norbixin, bixin, siphonaxanthin, and chlorophyll. These oil-soluble pigments may be used singly or in a combination of two or more.

(5-1-1-3) Oil-Soluble Physiological Active Substance

The oil-soluble physiological active substance (including liposoluble physiological active substances; the same applies below) usable in the present invention is not limited, as long as the oil-soluble physiological active substance is a biologically useful oil-soluble or liposoluble substance. The oil-soluble physiological active substance is preferably an edible substance that can be added to food or drink, or a substance that is applicable to a human body as a cosmetic.

The oil-soluble physiological active substance includes (i) oil-soluble medicinal agents; (ii) liposoluble vitamins, such as liver oil, vitamin A (e.g., retinol), vitamin A oil, vitamin D (e.g., ergocalciferol and cholecalciferol), vitamin $B_2$ butyric acid ester, ascorbic acid fatty acid ester, vitamin E (e.g., tocopherol and tocotrienol), and vitamin K (e.g., phylloquinone and menaquinone); (iii) plants essential oils, such as limonene, linalool, nerol, citronellol, geraniol, citral, 1-menthol, eugenol, cinnamic aldehyde, anethole, perillaldehyde, vanillin, and γ-undeca lactone; (iv) resveratrol, oil-soluble polyphenol, glucosylceramide, sesamin, phosphatidylserine, coenzyme $Q_{10}$, ubiquinol, and α-lipoic acid; (v) Ω-3 fatty acids, such as α-linolenic acid, eicosapentaenoic acid, and docosahexaenoic acid; (vi) Ω-6 fatty acids, such as linoleic acid and γ-linolenic acid; and (vii) steroids, such as plant sterols and animal sterols.

In particular, preferable examples of the oil-soluble physiological active substance include liposoluble vitamins; coenzyme $Q_{10}$; α-lipoic acid; and Ω-3 fatty acids, such as α-linolenic acid, eicosapentaenoic acid, and docosahexaenoic acid.

These oil-soluble physiological active substances may be used singly or in a combination of two or more.

(5-1-1-4) Other Oil-Soluble Materials

Examples of other oil-soluble materials usable in the present invention include elemi resin, mastic rosin, dammar resin, and ester gum.

(5-1-2) Oil Solvent (1-2)

The oil solvent is not particularly limited, as long as the oil solvent is usable as a solvent for the oil-soluble material or specifically is compatible with the oil-soluble material. The oil solvent is preferably an edible substance that can be added to food or drink, or a substance that is applicable to a human body as a cosmetic.

In the present specification, the term "fat and oil" can be understood as referring to a typical meaning on the basis of common technical knowledge. The terms "oil" and "fat" can be interpreted in an overlapping or integrated manner, in an interchangeable manner, or in a complementary manner, depending on the context.

The fat and oil includes (i) triacylglycerols, which are narrowly defined fat and oil; (ii) substances that share similar properties with triacylglycerols (i) and that are typically called oil (e.g., wax ester); and (iii) substances that contain these substances as a major component and that are typically called fat and oil.

In the present specification, "fat and oil" as an oil solvent are preferably liquid at 50° C. (preferably at 20° C.)

The oil solvent includes (i) vegetable oils, such as rapeseed oil, palm oil, soybean oil, olive oil, jojoba oil, coconut oil, safflower oil, corn oil, rice oil, sesame oil, linseed oil, cottonseed oil, and *perilla* oil; (ii) animal fat and oil, such as beef tallow, lard, and fish oil; (iii) sucrose acetate isobutylate (SAIB), glycerol fatty acid esters, and triglycerides (e.g., medium-chain triglycerides (MCT)). These examples may overlap with each other. These oil solvents may be used singly or in a combination of two or more.

In particular, preferable examples include glycerol fatty acid esters, triglycerides, sucrose acetate isobutylate, and vegetable oils; and more preferable examples include glycerol fatty acid esters and triglycerides (more preferably medium-chain triglycerides).

Medium-chain triglycerides (MCT) refer to triacylglycerols composed of medium-chain fatty acids having about 6 to 12 carbon atoms, preferably 6 to 10 carbon atoms, and more preferably 8 to 10 carbon atoms. Commercially available medium-chain triglycerides (MCT) can be used without any restriction. Specific examples include caprylic triglyceride, capric triglyceride, caprylic and capric triglyceride, and mixtures of these triglycerides.

Examples of glycerol fatty acid esters include polyglycerol fatty acid esters in which 5 to 8 molecules of $C_{2-10}$ saturated fatty acid are esterified to a polyglycerol having an average degree of polymerization of 3 to 10. A preferable average degree of polymerization of the polyglycerol for the glycerol fatty acid esters is 3 to 6. The saturated fatty acid is preferably $C_{6-10}$ saturated fatty acid, and more preferably $C_{8-10}$ saturated fatty acid. The glycerol fatty acid esters may be a single type or in a mixture of two or more.

Commercially available glycerol fatty acid esters may be used without any restriction. Examples include Salacos HG-8 (The Nisshin OilliO Group, Ltd.)

The oil solvent may optionally contain lecithin. The addition of lecithin can increase the effect provided by the dispersion method according to the present invention and can decrease the average particle size of emulsified particles generated by the dispersion method. The addition of lecithin can also contribute to the degree of transparency and storage stability of the emulsion composition generated by the dispersion method.

Lecithin is a liposoluble component containing phospholipid as the major component. The origin of lecithin is not particularly limited, and lecithin may be plant-derived lecithin, such as oilseed (e.g., soybean, rapeseed, and sunflower)-derived lecithin, or animal-derived lecithin, such as egg yolk. Lecithin usable in the present invention is preferably edible lecithin that can be added to food or drink, or lecithin that is applicable to a human body as a cosmetic. Lecithin usable in the present invention includes processed lecithin, such as fractionated lecithin, enzymatically hydrolyzed lecithin, and enzymatically treated lecithin. Lecithin, including processed lecithin, is commercially available. An example of such lecithin is SLP-white (trade name, Tsuji Oil Mills Co., Ltd.).

Lecithin is used in an amount of preferably 0.5 to 50 mass %, preferably 2 to 30 mass %, and more preferably 4 to 20 mass % relative to the oil phase component taken as 100 mass %. Lecithin is present in an amount of preferably 0.01 to 5 mass %, preferably 0.05 to 1 mass %, and more preferably 0.1 to 0.5 mass % in the emulsion composition taken as 100 mass %.

In the dispersion method according to the present invention, the oil-soluble material and the oil solvent are mixed to dissolve the oil-soluble material in the oil solvent, thereby preparing an oil phase component. This oil phase component is then finely dispersed in an aqueous solution containing predetermined gum ghatti as an emulsifier. This achieves emulsification of the oil phase component and the aqueous solution, and prepares an emulsion composition.

As will be understood from the description above by a person skilled in the art, one aspect of the dispersion method according to the present invention is an emulsification method described below, and another aspect of the dispersion method according to the present invention is a method for producing an emulsion composition described below.

In the present invention, the amount of the low-molecular gum ghatti according to the present invention is preferably 0.01 to 90 parts by mass, more preferably 0.01 to 60 parts by mass, and still more preferably 0.1 to 40 parts by mass, per 100 parts by mass of the aqueous liquid.

In the present invention, the amount of the low-molecular gum ghatti according to the present invention is preferably 1 to 1000 parts by mass, more preferably 5 to 1000 parts by mass, still more preferably 10 to 1000 parts by mass, even more preferably 20 to 1000 parts by mass, and particularly preferably 20 to 800 parts by mass, per 100 parts by mass of the water-insoluble substance.

In the present invention, the amount of the water-insoluble substance dispersed in the aqueous liquid is preferably 0.01 to 1000 parts by mass, more preferably 0.01 to 500 parts by mass, and still more preferably 0.1 to 250 parts by mass, per 100 parts by mass of the aqueous liquid.

(5-1-3) an Oil Solution of the Oil-Soluble Material Dissolved in the Oil Solvent (1-3)

The concentration of the oil-soluble material in the oil solution is not particularly limited. The upper limit is, for example, 90 mass %, 80 mass %, 70 mass %, 60 mass %, 50 mass %, 40 mass %, 30 mass %, 20 mass %, or 10 mass %; and the lower limit may be 1 mass %, 10 mass %, 20 mass %, 30 mass %, 40 mass %, 50 mass %, 60 mass %, 70 mass %, 80 mass %, or 90 mass %. The concentration of the oil-soluble material in the oil solution is, for example, 1 to 99 mass % or 1 to 90 mass %.

(5-2) Aqueous Liquid

In the present invention, the aqueous liquid is not particularly limited, and includes (2-1) water and (2-2) an aqueous solution.

(5-2-1) Water

Examples of water usable in the present invention include pure water, ion-exchanged water, and tap water.

(5-2-2) Aqueous Solution

The aqueous solution usable in the present invention may be a solution of a water-soluble material in water.

The form of the water-soluble material is not limited, and is, for example, a solid or a liquid.

Examples of the water-soluble material include water-soluble vitamins (e.g., vitamin C), polysaccharide thickeners, antioxidant agents, chelating agents, pH adjusters, excipients (e.g., dextrin), and alcohols.

Examples of alcohols include polyhydric alcohols, such as glycerin, diglycerin, triglycerin, polyglycerol, propylene glycol, dipropylene glycol, 1,3-butylene glycol, ethylene glycol, polyethylene glycol, sorbitol (D-sorbitol), xylitol, maltitol, erythritol, mannitol, xylose, glucose, lactose, mannose, oligotose, high-fructose corn syrup, and sucrose.

The water-soluble material may be a single type or a combination of two or more types.

The water-insoluble substance, the aqueous liquid, and the low-molecular gum ghatti according to the present invention can be mixed in any order.

The means or method, and the conditions for mixing the water-insoluble substance, the aqueous liquid, and the low-molecular gum ghatti according to the present invention are not particularly limited, as long as they are mixed. For example, a mixture liquid of the low-molecular gum ghatti according to the present invention and an aqueous liquid can be mixed with a water-insoluble substance.

The mixing operation may be performed with a known or commonly used mixing method. Examples include a method using a mixer, such as a homogenizer (e.g., a high-pressure homogenizer, a homogenizing disperser, a homomixer, a Polytron homogenizer, a colloid mill, and a Nanomizer), a propeller stirrer, or a paddle stirrer.

The mixing conditions can suitably be determined, depending on the type of mixer for use.

When the water-insoluble substance is a solid, examples of the mixing method include (1) a method in which the low-molecular gum ghatti according to the present invention, an aqueous liquid, and a solid water-insoluble substance are mixed, and then the water-insoluble substance in the mixture is pulverized; (2) a method in which a solid water-insoluble substance is pulverized beforehand, and then the pulverized solid is added to an aqueous liquid containing the low-molecular gum ghatti according to the present invention and mixed; and (3) combinations of these methods. The size of the dispersed solid water-insoluble substance can be adjusted by a commonly used method, such as adjusting the pulverization conditions.

When non-low-molecular gum ghatti, which is conventional gum ghatti, is used, it is difficult to disperse a water-insoluble substance in an aqueous liquid at a high concentration. In contrast, the low-molecular gum ghatti according to the present invention enables a water-insoluble substance to be dispersed in an aqueous liquid at a high concentration (e.g., 10 mass % or more, 15 mass % or more, 20 mass % or more, 25 mass % or more, 30 mass % or more, or 35 mass % or more). The upper limit of the content of the water-insoluble substance in the composition is, for example, 50 mass %, 40 mass %, or 35 mass %.

(6) Emulsification Method

As typically understood, the dispersion method according to the present invention can be an emulsification method, for example, when the water-insoluble substance is an oil liquid. The emulsification method according to the present invention comprises mixing an aqueous liquid, an oil liquid, and the low-molecular gum ghatti according to the present invention.

In the emulsification method according to the present invention, it is preferred that the oil liquid be a dispersoid, and that the aqueous liquid be a dispersion medium.

The means or method, and conditions for mixing the aqueous liquid, the oil liquid, and the low-molecular gum ghatti according to the present invention are not limited, as long as they can be mixed.

The aqueous liquid, the oil liquid, and the low-molecular gum ghatti according to the present invention can be mixed in any order.

Mixing itself may be an emulsification treatment, or mixing may be accompanied by an emulsification treatment.

The emulsification treatment may be performed with an emulsifying machine, such as a homogenizer (e.g., a high-pressure homogenizer, a homogenizing disperser, a homomixer, a Polytron stirrer, a colloid mill, and a Nanomizer).

The conditions for the emulsification treatment can be suitably determined, depending on the type of emulsifying machine for use.

In the present invention, the oil liquid is not particularly limited. Examples include at least one oil selected from the group consisting of soybean oil, cottonseed oil, safflower oil, corn oil, rice oil, coconut oil, *perilla* oil, sesame oil, linseed oil, palm oil, rapeseed oil, olive oil, jojoba oil, sardine oil, cod-liver oil, and medium-chain fatty acid triglycerides (MCT), and oil liquids containing these oils. In the present invention, the oil liquid may contain an oil-soluble substance.

The emulsification method according to the present invention provides emulsified particles having a median size (on a volume basis) of preferably 0.1 to 3 μm, more preferably 0.1 to 2 μm, still more preferably 0.1 to 1.5 μm, even more preferably 0.1 to 1.4 μm, particularly preferably 0.1 to 1.2 μm, and even more particularly preferably 0.1 to 1 μm.

(7) The Method for Producing a Dispersion Composition

The method for producing a dispersion composition comprises mixing an aqueous liquid, a water-insoluble substance, and the low-molecular gum ghatti according to the present invention. This production method can be understood from the description of the method for dispersing a water-insoluble substance according to the present invention above, and from other parts of the specification.

(8) The Method for Producing an Emulsion Composition

The present invention also provides a method for producing an emulsion composition using the low-molecular gum ghatti according to the present invention. The method for producing an emulsion composition according to the present invention comprises mixing an aqueous liquid, an oil liquid, and the low-molecular gum ghatti according to the present invention. This production method can be understood from the description of the emulsification method according to the present invention above, and from other parts of the specification.

(9) The Composition

The composition according to the present invention comprises the low-molecular gum ghatti according to the present invention. The content of the low-molecular gum ghatti according to the present invention in the composition may vary, for example, depending on the type and use of the composition. Specifically, when the composition is, for example, an emulsion preparation (e.g., emulsion flavorings, emulsion pigments, and emulsion physiological active substances), the content of the low-molecular gum ghatti according to the present invention in the composition may be 0.1 to 40 mass %, 0.5 to 20 mass %, or 1 to 15 mass %. When the composition is a food or drink, such as a drink product, the content of the low-molecular gum ghatti according to the present invention in the composition may be 0.01 to 5 mass %, 0.01 to 2 mass %, or 0.01 to 1 mass %. When the composition is, for example, an emulsifier or dispersant, the content of the low-molecular gum ghatti according to the present invention in the composition may be 0.0001 to 100 mass %.

The composition according to the present invention may comprise components other than the low-molecular gum ghatti according to the present invention. Examples include aqueous liquids, water-insoluble substances (e.g., oil liquids and water-insoluble solids), and water-soluble solids. Examples of the aqueous liquids include those described above. Examples of the water-insoluble substances and oil liquids include those described above.

The composition according to the present invention in an embodiment (embodiment 1) contains the low-molecular gum ghatti according to the present invention and a water-insoluble substance. The composition according to the present invention in another embodiment (embodiment 2) contains the low-molecular gum ghatti according to the present invention, an aqueous liquid, and a water-insoluble substance.

Examples of the form of the composition according to the present invention include liquids (e.g., solutions, emulsions, dispersions), semisolids (e.g., paste and cream), and solids (e.g., powders, granules, and tablets).

An embodiment (embodiment 1a) included in the embodiment (embodiment 1) of the composition according to the present invention can be a composition that can be prepared into the composition of embodiment 2, by adding an aqueous liquid thereto. The composition in embodiment 1a may be, for example, a composition obtained by removing some or all of the aqueous liquid from the composition in embodiment 2. Examples of the method for removing the aqueous liquid include commonly used water-removing methods, such as spray drying, freeze drying, use of an azeotropic solvent, and use of a water remover.

The composition according to the present invention in an embodiment is an emulsifier or a dispersant. The content of the low-molecular gum ghatti according to the present invention in the composition in this embodiment may vary, for example, depending on the type and use of the composition, and is preferably 0.0001 to 100 mass %, and more preferably 0.001 to 100 mass %.

The composition according to the present invention in an embodiment is a dispersion composition. This dispersion composition contains a water-insoluble substance, an aqueous liquid, and the low-molecular gum ghatti according to the present invention. In this dispersion composition, the water-insoluble substance is preferably dispersed in the aqueous liquid.

The content of the low-molecular gum ghatti in the dispersion composition may vary, depending on, for example, the type and use of the composition, and is, specifically, for example, 0.1 to 20 mass %, 0.5 to 15 mass %, 1 to 10 mass %, 0.01 to 5 mass %, 0.01 to 2 mass %, or 0.01 to 1 mass %.

The content of the water-insoluble substance in the composition is preferably 0.01 to 50 mass %, more preferably 0.1 to 45 mass %, and still more preferably 0.5 to 40 mass %.

As described above, the low-molecular gum ghatti according to the present invention, unlike non-low-molecular gum ghatti (conventional gum ghatti), enables a water-insoluble substance (preferably an oil liquid) to be dispersed in an aqueous liquid at a high concentration (e.g., an emulsification). Thus, the present invention can provide a composition in which a water-insoluble substance (preferably an oil liquid) is dispersed (preferably emulsified) in an aqueous liquid at a high concentration. The lower limit of the content of the water-insoluble substance (preferably oil liquid) in the composition is 20 mass % or more, 25 mass % or more, 30 mass % or more, or 35 mass % or more. The upper limit is, for example, 50 mass %, 40 mass %, or 35 mass %.

The content of fat and oil in the composition is preferably 0.01 to 50 mass %, more preferably 0.1 to 45 mass %, and still more preferably 0.5 to 40 mass %.

The content of an aqueous liquid in the composition is preferably 50 to 99.9 mass %, more preferably 65 to 99.9 mass %, and still more preferably 60 to 99 mass %.

The content of water in the composition is preferably 5 to 99.9 mass %, and more preferably 10 to 99.9 mass %.

The dispersion composition in an embodiment is an emulsion composition. In this emulsion composition, the water-insoluble substance is an oil liquid. In this emulsion composition, the oil liquid is preferably a dispersoid, and the aqueous liquid is a dispersion medium.

The emulsified particles contained in the emulsion composition have a median size (on a volume basis) of preferably 0.1 to 3 μm, more preferably 0.1 to 2 μm, still more preferably 0.1 to 1.5 μm, even more preferably 0.1 to 1.4 μm, particularly preferably 0.1 to 1.2 μm, and even more particularly preferably 0.1 to 1 μm.

The composition according to the present invention can stably retain a water-insoluble substance. The phrase "stably retain" means to decrease or prevent the aggregation of a water-insoluble substance prone to aggregation, and to decrease or prevent the evaporation (or volatilization) of a water-insoluble substance prone to evaporation (or volatilization).

The composition according to the present invention may be, for example, a food, a cosmetic or fragrance, a medical drug, or a quasi-drug.

Examples of the food include drinks, chewing gum, and all substances used in preparing, adjusting, or treating food (e.g., raw materials, intermediate products, and end products). In the present specification, the phrase "food or drink" includes food with health claims, food with function claims, food for specified health use, food with nutrient function claims, and food for special dietary uses. Examples of the perfumed product include toothpaste, shampoo, conditioners, body soap, and cosmetics. Examples of the medical drug and the quasi-drug include syrup preparations, drinkable preparations, tablets, capsules, tinctures, creams, and ointments.

EXAMPLES

The following describes the present invention in more detail with reference to Examples. However, the present invention is not limited to the Examples.

In the Examples, the following raw materials, instruments, and measurement methods were used.
(1) Raw Materials
Gum Ghatti: GATIFOLIA RD (trade name, San-Ei Gen F.F.I., Inc.)
Gum Arabic: Gum Arabic SD (trade name, San-Ei Gen F.F.I., Inc.)
Sucrose Acetate Isobutylate (SAIB): (trade name, Eastman Chemical Products, Inc.)
Medium-chain Triglyceride: "Sukore 64G" (trade name, The Nisshin OilliO Group, Ltd.)

In the present specification, the following abbreviation is also used.
SAIB: Sucrose Acetate Isobutylate
(2) Instrument and Analysis Method
(2-1) The Method for Measuring the Molecular Weight and Molecular Weight Distribution The molecular weight and molecular weight distribution were measured by GPC analysis under the following conditions.
Detector: RI
Mobile Phase: 100 mM $K_2SO_4$
Flow Rate: 1.0 ml/min
Temperature: 40° C.
Column: TSKgel GMPWXL 30 cm (Guard PWXL)
Injection: 100 μl
Pullulan Standard: Shodex STANDARD P-82
(2-2) Interfacial Activity Measurement Method The interfacial activity was determined by measuring the particle size of emulsified particles contained in the emulsion prepared in each Test Example with a laser diffraction/scattering particle size distribution analyzer, and determining the median size (on a volume basis).
(2-3) The Method for Measuring the Viscosity of a Gum Ghatti Aqueous Solution, and the Method for Measuring the Viscosity of a Gum Ghatti-Containing Emulsion
(2-3-1) Measurement Method a for the Viscosity of a Gum Ghatti Aqueous Solution
Measurement Method A 80 g of an 8 mass % aqueous solution of a gum ghatti sample (20° C.) was placed in a 100-ml screw bottle (inner diameter: 3.7 cm), and the viscosity was measured with the following instrument under the following conditions.
Instrument and Conditions
B-type Viscometer (Brookfield viscometer): rotor No. 2
Rotation Frequency: 60 rpm
Measurement Temperature: 20° C.
(2-3-2) Measurement Method B for the Viscosity of a Gum Ghatti Aqueous Solution
Measurement Method B 80 g of a 15 mass % aqueous solution of a gum ghatti sample (20° C.) was placed in a 100-ml screw bottle (inner diameter: 3.7 cm), and the viscosity was measured with the following instrument under the following conditions.
Instrument and Conditions
B-type Viscometer (Brookfield viscometer): rotor No. 2
Rotation Frequency: 30 rpm
Measurement Temperature: 20° C.
(2-3-3) Measurement Method C for the Viscosity of a Gum Ghatti Aqueous Solution
Measurement Method C 80 g of a 30 mass % aqueous solution of a gum ghatti sample (20° C.) was placed in a 100 ml-screw bottle (inner diameter: 3.7 cm), and the viscosity was measured with the following instrument under the following conditions.
Instrument and Conditions
B-type Viscometer (Brookfield viscometer): rotor No. 4
Rotation Frequency: 30 rpm
Measurement Temperature: 20° C.
(2-3-4) the Method for Measuring the Viscosity of a Gum Ghatti-Containing Emulsion 80 g of the emulsion prepared in each Test Example was placed in a 100-ml screw bottle (inner diameter: 3.7 cm), and the viscosity was measured with the following instrument under the following conditions.
Instrument and Conditions
B-type Viscometer: rotor No. 2
Rotation Frequency: 30 rpm
Measurement Temperature: 20° C.
(2-4) The Method for Measuring the Turbidity The turbidity of the emulsion prepared in each Test Example was measured at 720 nm with a spectrophotometer (cell: quartz cell 10 mm×10 mm). The measurement was performed with a water-dilution solution of the sample (emulsion) having a predetermined concentration (e.g., 0.1 mass % or 1 mass %).
(2-5) The Method for Measuring the Turbidity of an Aqueous Solution A 1 mass % aqueous solution of gum ghatti of each Test Example (20° C.) was prepared, and the turbidity (1% E) was measured at 720 nm with a spectrophotometer (cell: quartz cell 10 mm×10 mm).
(2-6) The Method for Measuring the Hunter Lab Color System of an Aqueous Solution A 1 mass % aqueous solution of gum ghatti of each Test Example (20° C.) was prepared, and the tristimulus values (value L, value a, and value b) of the Hunter Lab color system were measured with a colorimeter.
Instrument and Conditions
Colorimeter for juice: NDJ-300A (Nippon Denshoku Industries Co., Ltd.)
Hue measured by a reflected color method
(3) Terms The meanings of terms in the Test Examples are as follows.
D50 (μm), or particle size D50: median size (on a volume basis)
0.1% E (720 nm): the turbidity of a 0.1% water-dilution solution of a sample (emulsion) at 720 nm
1% E (720 nm): the turbidity of a 1% water-dilution solution of a sample (emulsion) at 720 nm Test Example 1: Production of Low-Molecular Gum Ghatti (Degradation in Autoclave) and Evaluation Preparation of Gum Ghatti Solution An 8% solution of each gum ghatti was prepared in accordance with the formulation of Table 1 by heating the mixture to 90° C. to dissolve gum ghatti.

TABLE 1

| Gum Ghatti | 8.0 mass % |
|---|---|
| Acid | Listed in Table 2 |
| Ion-exchanged Water | Balance |
| Total | 100.0 mass % |

TABLE 2

| Acid | Purity | Amount (mass) |
|---|---|---|
| Not added | — | 0.000 |
| Citric Acid | 100% | 0.200 |
| Phosphoric Acid | 85% | 0.120 |
| Phytic Acid | 50% | 0.687 |
| Malic Acid | 100% | 0.139 |
| Tartaric Acid | 100% | 0.156 |
| Hydrochloric Acid | 35% | 0.108 |
| Acetic Acid | 99.5% | 0.063 |
| Lactic Acid | 50% | 0.187 |
| Ascorbic Acid | 100% | 0.183 |

Molecular Weight Reduction Treatment

Each 8% gum ghatti solution was subjected to a degradation treatment in an autoclave (trade name: KS-323, Tomy Seiko Co., Ltd.) under the heating conditions shown in Tables 3 to 5 (temperature and time), thereby producing 8% low-molecular gum ghatti (or gum ghatti subjected to an autoclave treatment)-containing solutions of Examples 1 to 15, Comparative Example 2, and Examples 16 to 24. Additionally, an 8% gum ghatti-containing solution without the degradation treatment of Comparative Example 1 was prepared.

The 8% low-molecular gum ghatti (or gum ghatti subjected to an autoclave treatment)-containing solutions (samples for a test) were measured for the molecular weight, molecular weight distribution, and aqueous solution viscosity (with measurement method A for the viscosity of a gum ghatti aqueous solution). Tables 3 to 5 also show the results.

Preparation of Low-Molecular Gum Ghatti-Containing Emulsion 35 mass % of the 8% low-molecular gum ghatti (or gum ghatti subjected to an autoclave treatment)-containing solution, 10 mass % of medium-chain triglycerides, and 5 mass % of ion-exchanged water were placed in a 300-ml beaker and mixed with stirring using a triple propeller at a rotation speed of 1700 rpm for 3 minutes. 50 parts by mass of glycerin was further added thereto, and the result was mixed and stirred with a triple propeller at a rotation speed of 1700 rpm for 3 minutes.

The obtained mixture was subjected to an emulsification treatment with a high-pressure homogenizer (Nanomizer, perforation-type, Yoshida Kikai Co., Ltd.) at 45 MPa, 3 times, thereby obtaining a low-molecular gum ghatti (or gum ghatti subjected to an autoclave treatment)-containing emulsion. The same procedure was repeated to prepare a gum ghatti-containing emulsion of Comparative Example 1.

Analysis

The low-molecular gum ghatti (or gum ghatti subjected to an autoclave treatment)-containing emulsions, and the gum ghatti-containing emulsion of Comparative Example 1 (samples for a test) were measured for the interfacial activity, viscosity, and turbidity; and a storage test was performed. Tables 3 to 5 also show the results. As understood from the results, the produced low-molecular gum ghatti according to the present invention varied in the molecular weight, depending on the setting of conditions; and every low-molecular gum ghatti according to the present invention exhibited a high emulsifying capacity.

TABLE 3

| | | Comparative Example 1 | Example 1 | Example 2 | Example 3 | Example 4 | Example 5 | Example 6 | Example 7 | Example 8 |
|---|---|---|---|---|---|---|---|---|---|---|
| Acid | | — | — | — | — | — | — | — | — | — |
| Amount of Acid | mass % | 0 | 0 | 0 | 0 | 0 | 0 | 0 | 0 | 0 |
| Treatment Temperature | ° C. | — | 120 | 120 | 120 | 120 | 120 | 135 | 135 | 135 |
| Treatment Time | min | — | 5 | 10 | 15 | 30 | 60 | 15 | 30 | 60 |
| pH | | 4.5 | 4.4 | 4.4 | 4.5 | 4.5 | 4.4 | 4.4 | 4.3 | 4.2 |
| Viscosity of Aqueous Solution | mPa · s | 75.0 | 50.0 | 50.0 | 47.5 | 37.5 | 25.0 | 17.5 | 10.0 | 7.0 |
| GPC (RI) | Mw (mil.) | 1.372 | 1.042 | 1.008 | 0.899 | 0.705 | 0.547 | 0.342 | 0.197 | 0.096 |
| | Mn (mil.) | 0.090 | 0.156 | 0.148 | 0.129 | 0.095 | 0.073 | 0.050 | 0.032 | 0.018 |
| | Mw/Mn | 15.24 | 6.68 | 6.81 | 6.97 | 7.42 | 7.49 | 6.84 | 6.16 | 5.33 |
| Emulsification Test | D50 (μm) | 1.62 | 1.44 | 1.39 | 1.35 | 1.29 | 1.14 | 0.95 | 0.84 | 0.76 |
| | 0.1% E (720 nm) | 0.39 | 0.37 | 0.37 | 0.37 | 0.36 | 0.34 | 0.31 | 0.28 | 0.24 |
| | Viscosity (mPa · s) | 390 | 226 | 183 | 141 | 140 | 84 | 56 | 37 | 21 |
| 60° C. 3 Days | D50 (μm) | 1.55 | 1.40 | 1.38 | 1.36 | 1.30 | 1.15 | 0.96 | 0.84 | 0.76 |
| | 0.1% E (720 nm) | 0.40 | 0.39 | 0.39 | 0.39 | 0.39 | 0.35 | 0.33 | 0.29 | 0.26 |
| 60° C. 2 Weeks | D50 (μm) | 1.57 | 1.41 | 1.40 | 1.37 | 1.31 | 1.15 | 0.96 | 0.84 | 0.79 |
| | 0.1% E (720 nm) | 0.40 | 0.39 | 0.39 | 0.40 | 0.39 | 0.36 | 0.34 | 0.30 | 0.26 |

TABLE 4

| | | Example 9 | Example 10 | Example 11 | Example 12 | Example 13 | Example 14 | Example 15 | Comparative Example 2 |
|---|---|---|---|---|---|---|---|---|---|
| Acid | | Citric Acid | Citric Acid | Citric Acid | Citric Acid | Citric Acid | Citric Acid | Citric Acid | Citric Acid |
| Amount of Acid | mass % | 0.2 | 0.2 | 0.2 | 0.2 | 0.2 | 0.2 | 0.2 | 0.2 |
| Treatment Temperature | ° C. | 120 | 120 | 120 | 120 | 120 | 135 | 135 | 135 |

TABLE 4-continued

|  |  | Example 9 | Example 10 | Example 11 | Example 12 | Example 13 | Example 14 | Example 15 | Comparative Example 2 |
|---|---|---|---|---|---|---|---|---|---|
| Treatment Time | min | 5 | 10 | 15 | 30 | 60 | 15 | 30 | 60 |
| pH |  | 3.6 | 3.6 | 3.6 | 3.6 | 3.6 | 3.6 | 3.6 | 3.6 |
| Viscosity of Aqueous Solution | mPa·s | 22.5 | 27.5 | 15.5 | 12.5 | 10.0 | 7.5 | 5.0 | 4.5 |
| GPC (RI) | Mw (mil.) | 0.285 | 0.248 | 0.203 | 0.133 | 0.082 | 0.049 | 0.028 | 0.018 |
|  | Mn (mil.) | 0.091 | 0.082 | 0.070 | 0.050 | 0.031 | 0.017 | 0.010 | 0.005 |
|  | Mw/Mn | 3.13 | 3.02 | 2.90 | 2.66 | 2.65 | 2.88 | 2.80 | 3.60 |
| Emulsification Test | D50 (μm) | 0.99 | 0.90 | 0.79 | 0.72 | 0.59 | 0.57 | 0.72 | 10.39 |
|  | 0.1% E (720 nm) | 0.31 | 0.29 | 0.26 | 0.24 | 0.19 | 0.18 | 0.20 | 0.23 |
|  | Viscosity (mPa·s) | 70 | 63 | 52 | 41 | 30 | 23 | 19 | 23 |
| 60° C. 3 Days | D50 (μm) | 0.98 | 0.91 | 0.80 | 0.73 | 0.62 | 0.69 | 3.56 | 22.02 |
|  | 0.1% E (720 nm) | 0.32 | 0.30 | 0.27 | 0.25 | 0.21 | 0.22 | 0.35 | 0.18 |
| 60° C. 2 Weeks | D50 (μm) | 0.99 | 0.92 | 0.81 | 0.73 | 0.64 | 0.89 | 3.96 | 18.85 |
|  | 0.1% E (720 nm) | 0.33 | 0.31 | 0.26 | 0.26 | 0.21 | 0.23 | 0.36 | 0.18 |

TABLE 5

|  |  | Example 16 | Example 17 | Example 18 | Example 19 | Example 20 | Example 21 | Example 22 | Example 23 | Example 24 |
|---|---|---|---|---|---|---|---|---|---|---|
| Acid |  | Phytic Acid | Citric Acid | Lactic Acid | Ascorbic Acid | Phosphoric Acid | Malic Acid | Tartaric Acid | Acetic Acid | Hydrochloric Acid |
| Amount of Acid | mass % |  |  |  |  | Table 2 |  |  |  |  |
| Treatment Temperature | ° C. | 120 | 120 | 120 | 120 | 120 | 120 | 120 | 120 | 120 |
| Treatment Time | min | 15 | 15 | 15 | 15 | 15 | 15 | 15 | 15 | 15 |
| pH |  | 3.0 | 3.6 | 4.1 | 4.1 | 3.6 | 3.8 | 3.6 | 4.2 | 3.6 |
| Viscosity of Aqueous Solution | mPa·s | 10.0 | 15.0 | 25.0 | 25.0 | 15.0 | 17.5 | 17.5 | 32.5 | 17.5 |
| GPC (RI) | Mw (mil.) | 0.111 | 0.180 | 0.462 | 0.372 | 0.236 | 0.276 | 0.211 | 0.512 | 0.287 |
|  | Mn (mil.) | 0.022 | 0.067 | 0.061 | 0.052 | 0.040 | 0.044 | 0.055 | 0.062 | 0.045 |
|  | Mw/Mn | 5.05 | 2.69 | 7.57 | 7.15 | 5.90 | 6.27 | 3.84 | 8.26 | 6.38 |
| Emulsification Test | D50 (μm) | 0.67 | 0.77 | 1.08 | 0.96 | 0.84 | 0.91 | 0.85 | 1.20 | 0.90 |
|  | 0.1% E (720 nm) | 0.22 | 0.25 | 0.33 | 0.30 | 0.28 | 0.30 | 0.28 | 0.35 | 0.30 |
|  | Viscosity (mPa·s) | 35 | 49 | 155 | 78 | 40 | 63 | 55 | 100 | 60 |
| 60° C. 3 Days | D50 (μm) | 0.68 | 0.78 | 1.10 | 0.97 | 0.86 | 0.92 | 0.86 | 1.22 | 0.91 |
|  | 0.1% E (720 nm) | 0.23 | 0.26 | 0.35 | 0.32 | 0.29 | 0.31 | 0.29 | 0.37 | 0.31 |
| 60° C. 2 Weeks | D50 (μm) | 0.69 | 0.78 | 1.11 | 0.98 | 0.86 | 0.92 | 0.87 | 1.22 | 0.92 |
|  | 0.1% E (720 nm) | 0.23 | 0.27 | 0.35 | 0.32 | 0.29 | 0.31 | 0.30 | 0.37 | 0.31 |

Test Example 2: Comparative Example (Gum Arabic Subjected to an Autoclave Treatment)

For a comparative example, the procedure of Test Example 1 was repeated, except that gum arabic was subjected to an autoclave treatment under the conditions shown in Table 6, and evaluation was performed. Table 6 also shows the evaluation results. While the molecular weight of gum arabic slightly decreased due to heat treatment, the emulsifying capacity appeared to have instead slightly decreased.

TABLE 6

|  |  | Comparative Example 3 | Comparative Example 4 |
|---|---|---|---|
| Acid |  | — | — |
| Amount of Acid: mass % |  | 0 | 0 |
| Treatment Temperature: ° C. |  | — | 120 |
| Treatment Time: min |  | — | 60 |
| PH |  | 4.4 | 4.5 |
| Viscosity of Aqueous Solution: mPa·s |  | 10.0 | 10.0 |
| GPC (RI) | Mw (mil.) | 0.242 | 0.215 |
|  | Mn (mil.) | 0.080 | 0.075 |
|  | Mw/Mn | 3.03 | 2.87 |
| Emulsification Test | D50 (μm) | 2.22 | 2.07 |
|  | 0.1% E (720 nm) | 0.49 | 0.50 |
|  | Viscosity (mPa·s) | 34 | 32 |
| 60° C. 3 Days | D50 (μm) | 2.53 | 2.27 |
|  | 0.1% E (720 nm) | 0.45 | 0.44 |

TABLE 6-continued

|  |  | Comparative Example 3 | Comparative Example 4 |
|---|---|---|---|
| 60° C. 2 Weeks | D50 (μm) 0.1% E (720 nm) | 3.76 0.39 | 3.52 0.38 |

Test Example 3: Production Test of Low-Molecular Gum Ghatti (Degradation with Nanomizer) and Evaluation Preparation of Gum Ghatti Solution An 8% gum ghatti solution was prepared in accordance with the formulation of Table 7 by heating the mixture to 90° C. to dissolve gum ghatti.

TABLE 7

| Gum Ghatti | 8.0 mass % |
|---|---|
| Citric Acid (anhydrous) | 0.2 mass % |
| Ion-exchanged Water | 91.8 mass % |
| Total | 100.0 mass % |

Molecular Weight Reduction Treatment

Each 8% gum ghatti solution was subjected to a degradation treatment with a high-pressure homogenizer (Nanomizer, perforation-type, Yoshida Kikai Co., Ltd.) under the conditions shown in Table 8 (temperature, cycle, and pressure), thereby producing 8% low-molecular gum ghatti (or gum ghatti subjected to a Nanomizer treatment)-containing solutions of the Examples and Comparative Example.

The 8% low-molecular gum ghatti (or gum ghatti subjected to a Nanomizer treatment)-containing solutions (samples for a test) were measured for the molecular weight and aqueous solution viscosity (with measurement method A for the viscosity of a gum ghatti aqueous solution). Table 8 also shows the results.

Preparation of Low-Molecular Gum Ghatti-Containing Emulsion 3 mass % of orange essential oil, 0.8 mass % of medium-chain triglycerides, and 0.1 mass % of tocopherol were homogeneously mixed at room temperature, and 40 mass % of the 8% low-molecular gum ghatti solution and 5.6 mass % of water were added thereto, followed by mixing with stirring at room temperature (250 g of the mixture in a 300-ml beaker with a triple propeller at a speed of 1700 rpm for 3 minutes), thereby obtaining a mixture.

The obtained mixture was subjected to an emulsification treatment with a high-pressure homogenizer (Nanomizer, perforation-type, Yoshida Kikai Co., Ltd.) at 45 MPa, 4 times. 50.5 mass % of glycerin was added to the obtained emulsion and mixed, thereby obtaining a low-molecular gum ghatti (or gum ghatti subjected to a Nanomizer treatment)-containing emulsion.

For a comparative example, a gum ghatti-containing emulsion of Comparative Example 1a was prepared using the 8% gum ghatti-containing solution of Comparative Example 1.

Analysis

The low-molecular gum ghatti (or gum ghatti subjected to a Nanomizer treatment)-containing emulsions (samples for a test) were measured for the viscosity and turbidity. Table 8 also shows the results. As understood from the results, the produced low-molecular gum ghatti according to the present invention varied in the molecular weight even with the Nanomizer treatment, depending on the setting of conditions; and every low-molecular gum ghatti according to the present invention exhibited a high emulsifying capacity.

TABLE 8

|  |  | Comparative Example 1 | Example 25 | Example 26 | Example 27 | Example 28 | Example 29 | Example 30 | Example 31 | Example 32 | Example 33 | Example 34 |
|---|---|---|---|---|---|---|---|---|---|---|---|---|
| Treatment Temperature | ° C. | — | 60 | 60 | 60 | 80 | 80 | 80 | 20 | 20 | 20 | 20 |
| Treatment Cycle |  | — | 1 time | 3 times | 5 times | 1 time | 3 times | 5 times | 3 times | 5 times | 10 times | 20 times |
| Pressure (MPa) |  | — | 150 | 150 | 150 | 150 | 150 | 150 | 170 | 170 | 170 | 170 |
| GPC(RI) | Mw (mil.) | 1.37 | 0.52 | 0.43 | 0.38 | 0.53 | 0.46 | 0.39 | 0.39 | 0.33 | 0.27 | 0.23 |
| Viscosity of Aqueous Solution | mPa · s | 70 | 57 | 50 | 42 | 54.5 | 44.5 | 40.5 | 22 | 20 | 16.5 | 13.5 |
| After Emulsification | 1% E (720 nm) | 0.62 | 0.47 | 0.43 | 0.45 | 0.48 | 0.43 | 0.41 | 0.41 | 0.37 | 0.32 | 0.27 |
|  | Viscosity (mPa · s) | 277.5 | 215.5 | 200.0 | 173.0 | 231.0 | 183.5 | 170.5 | 148.0 | 121.5 | 91.0 | 70.0 |

Test Example 4-1: Production Test of Low-Molecular Gum Ghatti (Autoclave Treatment with Different Citric Acid Concentrations) and Evaluation The procedure of Test Example 1 was repeated with different citric acid concentrations and different gum ghatti concentrations shown in Table 9-1, thereby preparing gum ghatti solutions. These solutions were subjected to an autoclave treatment, thereby producing low-molecular gum ghatti-containing solutions. The low-molecular gum ghatti-containing solutions (samples for a test) were measured for the molecular weight. Table 9-1 also shows the results.

Preparation of Low-Molecular Gum Ghatti-Containing Emulsion 3 mass % of orange essential oil, 0.6 mass % of medium-chain triglycerides, 0.2 mass % of lecithin, and 0.1 mass % of tocopherol were mixed at room temperature; and 40 mass % of an 8 mass % gum ghatti aqueous solution and 5.6 mass % of ion-exchanged water were added thereto, thereby preparing a mixture. The obtained mixture was subjected to an emulsification treatment with a high-pressure homogenizer (Nanomizer, perforation-type, Yoshida Kikai Co., Ltd.) at 45 MPa, 4 times. 50.5 mass % of glycerin was added to the obtained emulsion and mixed, thereby obtaining a low-molecular gum ghatti (or gum ghatti subjected to an autoclave treatment)-containing emulsion.

For a comparative example, a gum ghatti-containing emulsion was prepared using the 8% gum ghatti-containing solution of Comparative Example 1.

Analysis

The low-molecular gum ghatti (or gum ghatti subjected to an autoclave treatment)-containing emulsions (samples for a test) were measured for the viscosity and turbidity; and a storage test was performed. Table 9-1 also shows the results.

TABLE 9-1

|  |  | Comparative Example 1 | Example 35 | Example 36 | Example 37 | Example 38 | Example 39 | Example 40 | Example 41 |
|---|---|---|---|---|---|---|---|---|---|
| Treatment Temperature | ° C. | No Treatment | 120 | 120 | 120 | 120 | 120 | 120 | 120 |
| Treatment Time |  | 0 min | 15 min | 15 min | 15 min | 15 min | 15 min | 15 min | 15 min |
| Concentration of Gum Ghatti | mass % | 8 | 8 | 15 | 20 | 30 | 30 | 30 | 30 |
| Concentration of Citric Acid (anhydrous) | mass % | — | 0.2 | 0.375 | 0.5 | 0.75 | 1.5 | 3.0 | 6.0 |
| GPC (RI) | Mw (mil.) | 1.372 | 0.169 | 0.182 | 0.179 | 0.189 | 0.139 | 0.084 | 0.049 |
| After Emulsification | 1% E (720 nm) | 0.62 | 0.29 | 0.29 | 0.32 | 0.30 | 0.28 | 0.24 | 0.23 |
|  | Viscosity (mPa · s) | 277.5 | 52.5 | 53.5 | 42.0 | 55.0 | 47.0 | 32.0 | 25.5 |
| Storage at 60° C. for 4 Days | 1% E (720 nm) | 0.653 | 0.37 | 0.37 | 0.38 | 0.37 | 0.35 | 0.31 | 0.30 |
| Storage at 5° C. for 3 Months | 1% E (720 nm) | 0.635 | 0.31 | 0.31 | 0.34 | 0.32 | 0.30 | 0.26 | 0.25 |
| Storage at 25° C. for 3 Months | 1% E (720 nm) | 0.688 | 0.35 | 0.35 | 0.37 | 0.37 | 0.34 | 0.30 | 0.29 |

Test Example 4-2: Viscosity of Gum Ghatti Aqueous Solution

Aqueous solutions of non-molecular-weight-reduced gum ghatti (GATIFOLIA RD), non-molecular-weight-reduced gum ghatti (Gum Ghatti SD), and low-molecular gum ghatti of the Examples shown in the tables were measured for the viscosity. The aqueous solutions were measured with both measurement method B and C for the viscosity of a gum ghatti aqueous solution. Table 9-2 shows the results.

TABLE 9-2

|  | Viscosity (Measurement Method B) mPa · s | Viscosity (Measurement Method C) mPa · s |
|---|---|---|
| Non-molecular-weight-reduced Gum Ghatti GATIFOLIA RD (Molecular Weight: 1.20 million) | 455 | 19100 |
| Non-molecular-weight-reduced Gum Ghatti Gum Ghatti SD (Molecular Weight: 1.36 million) | 267 | 10040 |
| Example 18 (Molecular Weight: 462 thousand) | 45 | 700 |
| Example 9 (Molecular Weight: 285 thousand) | 26 | 520 |
| Example 17 (Molecular Weight: 180 thousand) | 28 | 320 |
| Example 12 (Molecular Weight: 133 thousand) | 14 | 160 |

Test Example 4-3: Optical Properties of Gum Ghatti Aqueous Solution

Aqueous solutions of non-molecular-weight-reduced gum ghatti (Gum Ghatti SD), and low-molecular gum ghatti of the Examples shown in the tables were prepared. The turbidity and color system (Hunter Lab color system) of the aqueous solutions were measured. Table 9-3 shows the results.

TABLE 9-3

|  | Turbidity of 1% Aqueous Solution | Color System Value L | Value a | Value b |
|---|---|---|---|---|
| Non-molecular-weight-reduced Gum Ghatti Gum Ghatti SD (Molecular Weight: 1.36 million) | 0.017 | 78.2 | −3.2 | 15.7 |
| Example 9 (Molecular Weight: 285 thousand) | 0.029 | 76.6 | −2.4 | 17.8 |
| Example 17 (Molecular Weight: 180 thousand) | 0.049 | 77.1 | −3.0 | 18.9 |
| Example 12 (Molecular Weight: 133 thousand) | 0.040 | 83.9 | −4.2 | 8.5 |

Test Example 5: Applied Test 1 (Production of High-Concentration Carotenoid Pigment-Containing Preparation and Evaluation)

Preparation of Gum Ghatti Solution

An 8% gum ghatti solution was prepared in accordance with the formulation of Table 10 by heating the mixture to 90° C. to dissolve gum ghatti.

TABLE 10

| | |
|---|---|
| Gum Ghatti | 8.0 mass % |
| Citric Acid (anhydrous) | 0.2 mass % |
| Ion-exchanged Water | 91.8 mass % |
| Total | 100.0 mass % |

Molecular Weight Reduction Treatment

The 8% gum ghatti solution was subjected to a degradation treatment in an autoclave (at 120° C. for 15 minutes), thereby producing an 8% low-molecular gum ghatti-containing solution ("solution of Production Example W"). Additionally, an 8% low-molecular gum ghatti-containing solution without the degradation treatment was prepared ("solution of Comparative Production Example R").

Both 8% gum ghatti-containing solutions (samples for a test) were measured for the molecular weight, and Table 11 shows the results.

Preparation of Low-Molecular Gum Ghatti-Containing Emulsion 3.2 mass % of medium-chain triglycerides, 40 mass % of am 8 mass % gum ghatti aqueous solution, and 56.8 mass % of ion-exchanged water were stirred at room temperature, thereby obtaining a mixture. The obtained mixture was subjected to an emulsification treatment with a high-pressure homogenizer (Nanomizer, perforation-type, Yoshida Kikai Co., Ltd.) at 50 MPa, 4 times, thereby obtaining a low-molecular gum ghatti (or gum ghatti subjected to an autoclave treatment)-containing emulsion.

Analysis

The low-molecular gum ghatti (or gum ghatti subjected to an autoclave treatment)-containing emulsion (a sample for a test) was measured for the median size (on a volume basis) of emulsified particles and the turbidity. Table 11 shows the results.

TABLE 11

| | | Solution of Production Example W | Solution of Comparative Production Example R |
|---|---|---|---|
| Weight Average Molecular Weight (Mw) (mil.) | | 0.197 | 1.372 |
| Evaluation Results of Interfacial Activity | 1% E (720 nm) | 0.179 | 0.229 |
| | Particle Size D50 (μm) | 0.240 | 0.300 |

Powderization

The solution of Production Example W was formed into a powder with a spray dryer, thereby obtaining a low-molecular gum ghatti-containing powder of Production Example W. In the same manner, a powder of Comparative Production Example R was obtained from the solution of Comparative Production Example R.

Preparation of High-Concentration Carotenoid Pigment-Containing Preparation

Using the prepared gum ghatti powder (the powder of Production Example W or the powder of Comparative Production Example R), a carotenoid pigment-containing preparation (preparation R1 of the Comparative Example and preparations W1 and W2 of the Examples) of the formulations of Table 12 was prepared as described below.

The raw materials shown in section (1) of Table 12 were heated to 158° C. to dissolve the carotene. The raw materials shown in section (2) of Table 12 were added to the obtained solution and mixed with stirring. The raw material in section (3) of Table 12 (i.e., water) was then added to the mixture and mixed with stirring.

The mixture was treated with a high-pressure homogenizer (Nanomizer, perforation-type, Yoshida Kikai Co., Ltd.) at 50 MPa, 3 times, and then the raw material in section (4) of Table 12 (i.e., glycerin) was added thereto, followed by stirring for homogenization.

The powder solution of Comparative Production Example R in Table 12, was prepared by mixing 79.5 mass % of ion-exchanged water, 0.5 mass % of citric acid (anhydrous), and 20 mass % of the powder of Comparative Production Example R at 90° C. for 30 minutes. The powder solution of Production Example W was prepared by mixing 80 mass % of ion-exchanged water and 20 mass % of the powder of Production Example W at 90° C. for 30 minutes.

TABLE 12

| | | (mass %) | | |
|---|---|---|---|---|
| Raw Materials | | Preparation R1 | Preparation W1 | Preparation W2 |
| (1) | Suspension of β-carotene in Medium-chain Triglycerides (β-Carotene Content: 31.14%) | 4.39 | 4.39 | 2.20 |
| | Tocopherol | 0.20 | 0.20 | 0.20 |
| | Medium-chain Triglycerides | 4.13 | 4.13 | 1.96 |
| | SAIB | 5.28 | 5.28 | 2.64 |
| (2) | Powder Solution of Comparative Production Example R | 20.00 | — | — |
| | Powder Solution of Production Example W | — | 20.00 | 37.00 |
| | Water | 9.75 | 9.75 | 8.17 |
| | L-Ascorbic Acid | 0.50 | 0.50 | 0.50 |
| | Citric Acid (anhydrous) | 0.25 | 0.25 | 0.25 |
| (3) | Water | 10.4 | 10.40 | |
| (4) | Glycerin | 45.10 | 45.10 | 47.08 |
| | | 100.00 | 100.00 | 100.00 |

These preparations were measured for the median size of emulsified particles (on a volume basis) and the turbidity (720 nm), and a test for examining the change over time was also conducted. The turbidity was measured by preparing a 0.1 mass % water-dilution solution of the obtained preparation and measuring the turbidity of the water-dilution solution at 720 nm with a spectrophotometer (cell: quartz cell, 10 mm×10 mm). Table 13 shows the results.

As understood from the results, the preparations containing the low-molecular gum ghatti according to the present invention exhibited high stability of the emulsified particles. Preparation W2 containing the low-molecular gum ghatti according to the present invention exhibited a median size of the emulsified particles as extremely small as 0.15 μm; thus, the use of this preparation can provide a highly transparent composition.

TABLE 13

| Storage Temperature for Preparation | | Storage Period | | | | | | | | | |
|---|---|---|---|---|---|---|---|---|---|---|---|
| | | Immediately after Preparation | | 1 Day | | 2 Weeks | | 1 Month | | 3 Months | |
| | | D50 | 0.1% E | D50 | 0.1% E | D50 | 0.1% E | D50 | 0.1% E | D50 | 0.1% E |
| | °C. | (μm) | (720 nm) | (μm) | (720 nm) | (μm) | (720 nm) | (μm) | (720 nm) | (μm) | (720 nm) |
| Preparation R1 | 5 | 0.48 | 0.413 | — | — | — | — | 0.50 | 0.422 | 0.49 | 0.422 |
| | 25 | | | — | — | — | — | 0.50 | 0.427 | 0.50 | 0.431 |
| | 40 | | | — | — | — | — | 0.50 | 0.433 | — | — |
| | 60 | | | 0.50 | 0.428 | 0.52 | 0.432 | — | — | — | — |
| Preparation W1 | 5 | 0.39 | 0.354 | — | — | — | — | 0.40 | 0.362 | 0.40 | 0.362 |
| | 25 | | | — | — | — | — | 0.41 | 0.364 | 0.41 | 0.368 |
| | 40 | | | — | — | — | — | 0.41 | 0.372 | — | — |
| | 60 | | | 0.41 | 0.367 | 0.43 | 0.375 | — | — | — | — |
| Preparation W2 | 5 | 0.15 | 0.055 | — | — | — | — | 0.15 | 0.057 | 0.15 | 0.057 |
| | 25 | | | — | — | — | — | 0.15 | 0.059 | 0.15 | 0.061 |
| | 40 | | | — | — | — | — | 0.15 | 0.061 | — | — |
| | 60 | | | 0.15 | 0.057 | 0.16 | 0.066 | — | — | — | — |

Test Example 6: Applied Test 2 (Production of High-Concentration Oil-Containing Preparation and Evaluation)

Using the gum ghatti powder prepared in Test Example 5 (Powder of Production Example W or Powder of Comparative Production Example R), orange flavoring preparations of the formulations shown in Table 14 (preparation R2 of the Comparative Example and preparations W3 to W5 of the Examples) were prepared as described below.

The raw materials in sections (2) and (3) of Table 14 were mixed with stirring. The raw materials in section (1) of Table 14 were heated to 100° C., and the mixture of the raw materials in sections (2) and (3) was added thereto, followed by mixing with stirring. The mixture was treated with a high-pressure homogenizer (Nanomizer, perforation-type, Yoshida Kikai Co., Ltd.) at 50 MPa, 3 times for homogenization. The powder solution of Comparative Production Example R in Table 14 was prepared by mixing 79.5 mass % of ion-exchanged water, 0.5 mass % of citric acid (anhydrous), and 20 mass % of the powder of Comparative Production Example R at 90° C. for 30 minutes. The powder solution of Production Example W was prepared by mixing 80 mass % of ion-exchanged water and 20 mass % of the powder of Production Example W at 90° C. for 30 minutes.

TABLE 14

| | | (mass %) | | | |
|---|---|---|---|---|---|
| Raw Materials | | Preparation R2 | Preparation W3 | Preparation W4 | Preparation W5 |
| (1) | Tocopherol | 0.20 | 0.20 | 0.20 | 0.20 |
| | Medium-chain Triglycerides | 7.95 | 7.95 | 9.49 | 11.02 |
| | SAIB | 9.85 | 9.85 | 12.31 | 14.78 |
| | Orange Essential Oil | 2 | 2 | 3 | 4 |

TABLE 14-continued

| | | (mass %) | | | |
|---|---|---|---|---|---|
| Raw Materials | | Preparation R2 | Preparation W3 | Preparation W4 | Preparation W5 |
| (2) | Powder Solution of Comparative Production Example R | 24.50 | — | — | — |
| | Powder Solution of Production Example W | — | 24.50 | 39.50 | 39.50 |
| | Citric Acid (anhydrous) | 0.50 | 0.50 | 0.50 | 0.50 |
| (3) | Water | 19.55 | 19.55 | 3.25 | 0.75 |
| | Glycerin | 35.45 | 35.45 | 31.75 | 29.25 |
| | | 100.00 | 100.00 | 100.00 | 100.00 |

These preparations were measured for the median size (on a volume basis) of emulsified particles and the turbidity, and a test for examining the change over time was conducted. The turbidity was measured by preparing a 0.1 mass % water-dilution solution of each obtained preparation and measuring the turbidity of the water-dilution solution at 720 nm with a spectrophotometer (cell: quartz cell 10 mm×10 mm). Table 15 shows the results. As understood from the results, preparations containing the low-molecular gum ghatti according to the present invention exhibited high stability of the emulsified particles. Preparations W4 and W5 had a significantly high content of oil phase (section (1)) (25 mass % and 30 mass %), and such a high oil phase content would have made it difficult to prepare an emulsion preparation using a conventional gum ghatti. However, the use of the low-molecular gum ghatti according to the present invention enabled the production of a preparation with highly stable emulsified particles.

TABLE 15

| Storage Temperature for Preparation | Immediately after Preparation | | 1 Day | | 2 Weeks | | 1 Month | | 3 Months | |
|---|---|---|---|---|---|---|---|---|---|---|
| | D50 | 0.1% E | D50 | 0.1% E | D50 | 0.1% E | D50 | 0.1% E | D50 | 0.1% E |
| °C. | (μm) | (720 nm) | (μm) | (720 nm) | (μm) | (720 nm) | (μm) | (720 nm) | (μm) | (720 nm) |
| Preparation R2  5 | 0.66 | 0.406 | — | — | — | — | 0.66 | 0.414 | 0.66 | 0.418 |
| 25 | | | — | — | — | — | 0.67 | 0.420 | 0.67 | 0.43 |
| 40 | | | — | — | — | — | 0.67 | 0.428 | — | — |
| 60 | | | 0.67 | 0.415 | 0.68 | 0.437 | — | — | — | — |
| Preparation W3  5 | 0.53 | 0.341 | — | — | — | — | 0.53 | 0.349 | 0.53 | 0.351 |
| 25 | | | — | — | — | — | 0.54 | 0.354 | 0.54 | 0.359 |
| 40 | | | — | — | — | — | 0.54 | 0.361 | — | — |
| 60 | | | 0.54 | 0.351 | 0.56 | 0.37 | — | — | — | — |
| Preparation W4  5 | 0.53 | 0.422 | — | — | — | — | 0.53 | 0.437 | 0.53 | 0.349 |
| 25 | | | — | — | — | — | 0.53 | 0.444 | 0.54 | 0.447 |
| 40 | | | — | — | — | — | 0.54 | 0.449 | — | — |
| 60 | | | 0.54 | 0.44 | 0.55 | 0.467 | — | — | — | — |
| Preparation W5  5 | 0.60 | 0.589 | — | — | — | — | 0.60 | 0.605 | 0.60 | 0.6 |
| 25 | | | — | — | — | — | 0.60 | 0.605 | 0.61 | 0.61 |
| 40 | | | — | — | — | — | 0.61 | 0.618 | — | — |
| 60 | | | 0.61 | 0.665 | 0.62 | 0.623 | — | — | — | — |

Test Example 7: Applied Test 3 (Production of Transparent, Marigold Pigment-Containing Preparation and Evaluation)

Using the solution of Production Example W prepared in Test Example 5 (an 8 mass % solution of low-molecular gum ghatti having a molecular weight of 197,000), a marigold pigment-containing preparation of the formulation shown in Table 16 was prepared as described below.

The raw materials in section (2) of Table 16 were mixed with stirring, and then the raw materials in section (3) were added thereto, followed by stirring. The raw materials in section (1) of Table 16 were heated to 120° C., and the mixture of the raw materials of sections (2) and (3) was added thereto, followed by mixing with stirring. The mixture was filtered (100-mesh), and then treated with a high-pressure homogenizer (Nanomizer, perforation-type, Yoshida Kikai Co., Ltd.) at 50 MPa·s, 4 times, for homogenization.

TABLE 16

| Raw Materials | | (mass) |
|---|---|---|
| (1) | Marigold Oil Color Value: 4500 (Marigold Oil No. 84790)* | 0.57 |
| | Medium-chain Triglycerides | 2.48 |
| | SAIB | 1.75 |
| | Tocopherol | 0.20 |
| (2) | Solution of Production Example W | 40.00 |
| | Citric Acid (anhydrous) | 0.50 |
| | L-Ascorbic Acid | 0.50 |
| (3) | Water | 12.14 |
| | Glycerin | 41.86 |
| | | 100.00 |

The asterisk "*" denotes a product of San-Ei Gen F.F.I., Inc.

The prepared marigold pigment-containing preparation was measured for the median size (on a volume basis) of emulsified particles and the turbidity (at 720 nm). The turbidity was measured by preparing a 1% water-dilution solution of the obtained preparation and measuring the turbidity of the water-dilution solution at 720 nm with a spectrophotometer (cell: quartz cell 10 mm×10 mm). Table 17 shows the results. As understood from the results, the preparation containing the low-molecular gum ghatti according to the present invention exhibited an emulsified particle size as small as 0.13 μm, and a transparent emulsion composition was confirmed to have been prepared.

TABLE 17

| | Test Example 7 |
|---|---|
| D50 (nm) | 0.132 |
| 1% E (720 nm) | 0.093 |

Test Example 8: Applied Test 4 (Production of Water-Insoluble Substance-Containing Dispersion Composition and Evaluation)

Using the solution of Production Example W prepared in Test Example 5 (an 8 mass % solution of low-molecular gum ghatti having a molecular weight 197,000), a lycopene-dispersed preparation of the formulation shown in Table 18 was prepared as described below.

The lycopene pulverized portion of the raw materials in section (1) of Table 18 was prepared by adding 20 g of crystalline lycopene to 180 g of 70% ethanol and pulverizing the mixture with a wet-milling machine Dyno-Mill (WAB, Dyno-Mill) for 1 hour to prepare a pulverized lycopene product. The raw materials in section (3) of Table 18 were mixed with stirring, and the raw material in section (2) was added thereto, followed by stirring. The raw material in section (1) was added to the mixture of the raw materials (2) and (3), and mixed with stirring. This mixture was treated with a high-pressure homogenizer (Nanomizer, perforation-type, Yoshida Kikai Co., Ltd.) at 50 MPa·s, 5 times, for homogenization.

TABLE 18

|   | Raw Materials | (mass %) |
|---|---|---|
| (1) | Lycopene Pulverized Portion (Lycopene Content: 9.3 mass %) | 11.34 |
| (2) | Solution of Production Example W | 24.00 |
| (3) | Citric Acid | 0.45 |
|   | Ascorbic Acid | 0.90 |
|   | Water | 57.88 |
| (4) | Propylene Glycol | 5.43 |
|   |   | 100.00 |

The prepared lycopene-dispersed preparation (lycopene content: 1 mass %) was measured for the following: the median size of dispersed particles (on a volume basis, μm), the frequency of particles having a particle size of 1.8 μm or more (%), and the frequency of particles having a particle size of 0.6 μm or more (%).

Measurement Instrument

Laser diffraction particle size distribution: Microtrac MT3000, MicrotracBEL Corp.

Table 19 shows the results. As understood from the results, the preparation containing the low-molecular gum ghatti according to the present invention did not exhibit aggregation of particles immediately after the production or after storage at 60° C. for 13 days, and was confirmed to be excellent in dispersion stability.

TABLE 19

|   | Immediately after Production | After Storage at 60° C. for 13 Days |
|---|---|---|
| D50 (μm) | 0.244 | 0.243 |
| 1.8 μm or more (%) | 0.00 | 0.00 |
| 0.6 μm or more (%) | 4.35 | 4.52 |

Test Example 9: Applied Test 5 (Production of High-Concentration Menthol-Containing Powdery Flavoring Preparation and Evaluation)

Using the solution of Production Example W prepared in Test Example 5 (an 8 mass % solution of low-molecular gum ghatti having a molecular weight 197,000), a powdery menthol preparation of the formulation shown in Table 20 was prepared as described below.

The three substances in section (1) of table 20 were homogeneously mixed. The raw material in section (3) of Table 20 was added to the raw materials in section (2) of Table 20 while stirring, and the mixture was heated and dissolved, followed by cooling. The raw material mixture of section (1) of Table 20 was added to the mixture of the raw materials in sections (2) and (3), and mixed with stirring. The mixture was then treated with a high-pressure homogenizer (Nanomizer, perforation-type, Yoshida Kikai Co., Ltd.) at 50 MPa·s, 5 times, for homogenization. The obtained homogeneous mixture was subjected to spray drying with a spray dryer (spray dryer, APV Nordic Anhydro) (inlet temperature: 140° C., outlet temperature: 80° C.), thereby obtaining a menthol-containing powdery flavoring preparation, from which the moisture content had been removed.

TABLE 20

|   | Raw Materials | (parts by mass) |
|---|---|---|
| (1) | Menthol | 40.00 |
|   | Lecithin | 1.00 |
|   | Medium-chain Triglycerides | 1.00 |
| (2) | Solution of Production Example W | 125.00 |
|   | Water | 85.00 |
| (3) | Dextrin | 48.00 |
|   |   | 300.00 |

The prepared menthol-containing powdery flavoring preparation was measured for the percentage of residual menthol, and a menthol sublimation test was conducted.

Measurement of Residual Menthol Percentage 0.2 g of the prepared menthol-containing powdery flavoring preparation was precisely weighed with a 100-ml measuring flask, and 50 ml of pure water was added thereto to dissolve the preparation, followed by an ultrasound treatment with an ultrasonic bath (SU-2TH, Sibata Scientific Technology Ltd.) for 3 minutes. Subsequently, 25 ml of acetone was added, and the mixture was again subjected to an ultrasound treatment for 3 minutes. 5 ml of an internal standard solution (a 1% 1-octanol:acetone solution) was added thereto, and the volume was precisely adjusted to 100 ml with acetone. This solution was filtered through a 0.5-μm filter, thereby obtaining a filtrate as a test solution.

Separately, 0.8 g of 1-menthol was precisely weighed with a 100-ml measuring flask, and the volume was precisely adjusted to 100 ml with acetone. 3 ml, 5 ml, 8 ml, and 12 ml of this solution were precisely measured with a 100-ml measuring flask; and 50 ml of pure water, 25 ml of acetone, and 5 ml of an internal standard solution were added thereto and quantified to 100 ml with acetone in the same manner as in the preparation method for the test solution. This solution was filtered through a 0.5-μm filter, thereby obtaining a filtrate as a solution for calibration.

These test solutions and the solution for calibration were tested by gas chromatography, and menthol was quantified by an internal standard method. The percentage of residual menthol was determined by the following formula: (the amount of the obtained residual menthol/the amount of menthol used)×100. Table 21 shows the results. The prepared menthol-containing powdery flavoring preparation exhibited a residual menthol percentage as high as 90.8%.

TABLE 21

|   | Test Example 9 |
|---|---|
| Residual Percentage (%) = (actual value/stoichiometric value) × 100 | 90.8% |

Sublimation Test

In this sublimation test, the prepared menthol-containing powdery flavoring preparation was placed in a 100-ml colorless transparent glass tube such that the menthol concentration was 1000 ppm (w/v), and the glass tube was sealed, followed by storage in a thermostatic apparatus at 60° C. for 3 hours. Thereafter, the preparation was cooled to room temperature (20° C.), and whether crystals of menthol were precipitated in the glass tube was examined. In this sublimation test, the precipitates of crystalline menthol were not confirmed.

As understood from the results, the menthol-containing powdery flavoring preparation prepared using the low-molecular gum ghatti according to the present invention was confirmed to exhibit excellent stability in retaining a highly volatile flavoring component.

The invention claimed is:

1. A low-molecular gum ghatti having
    a weight average molecular weight within a range of $0.040 \times 10^6$ to $0.60 \times 10^6$ and
    a molecular weight distribution, which is a ratio of the weight average molecular weight to a number average molecular weight, within a range of 1.1 to 10.

2. The low-molecular gum ghatti according to claim 1, whose emulsified particles have a median size, on a volume basis, within a range of 0.1 to 1.5 µm,
    the median size being measured by an interfacial activity measurement method as follows:
    (1) 10 mass % of a medium-chain triglyceride, 35 mass % of an 8 mass % gum ghatti aqueous solution, and 5 mass % of ion-exchanged water are stirred at room temperature, and 50 mass % of glycerol is added thereto to prepare a mixture;
    (2) the mixture is subjected to an emulsification treatment at 45 MPa three times with a high-pressure homogenizer to obtain an emulsion; and
    (3) a particle size of emulsified particles contained in the emulsion is measured with a laser diffraction/scattering particle size distribution analyzer to determine the median size on a volume basis.

3. A composition comprising the low-molecular gum ghatti of claim 1.

* * * * *